United States Patent [19]

Levine

[11] 4,420,353
[45] Dec. 13, 1983

[54] METHOD OF MAKING A STOOL SAMPLING DEVICE

[76] Inventor: Robert A. Levine, 31 Pilgrim La., Guilford, Conn. 06437

[21] Appl. No.: 266,151

[22] Filed: May 22, 1981

Related U.S. Application Data

[63] Continuation-in-part of Ser. No. 110,437, Jan. 7, 1980, Pat. No. 4,273,741, and Ser. No. 203,083, Nov. 3, 1980, Pat. No. 4,367,750.

[51] Int. Cl.³ .................... G01N 1/02; G01N 33/52; G01N 33/72
[52] U.S. Cl. .................................. 156/227; 156/250; 156/252; 156/268; 156/324; 156/324.4; 128/638; 422/56; 422/61
[58] Field of Search ............. 156/226, 227, 252, 268, 156/324, 324.4, 250; 128/283, 638; 422/56, 61

[56] References Cited

U.S. PATENT DOCUMENTS

| 4,120,715 | 10/1978 | Ockwell | 128/283 |
| 4,163,039 | 7/1979 | Emrich | 422/56 |
| 4,259,964 | 4/1981 | Levine | 128/283 |
| 4,273,741 | 6/1981 | Levine | 128/283 |

Primary Examiner—Caleb Weston
Attorney, Agent, or Firm—Kevin B. Clarke

[57] ABSTRACT

The stool sampling device is a pliant laminate which can be used to obtain direct anal stool smears for use in testing for occult blood in the stool. Predetermined fold lines are disposed on the laminate, and combine with linear adhesive strips so that, after the stool smear is on the device, the laminate can be folded quickly and easily into a closed pouch. The adhesive is preferably releasable so that the pouch can be reopened for stool testing purposes. The stool-receiving layer of the pliant laminate may be removed, if desired, from the remainder of the device to be used in special chromatographic testing of the stool specimen.

3 Claims, 7 Drawing Figures

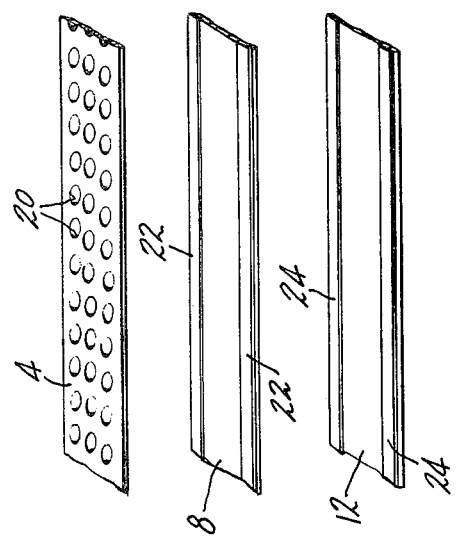
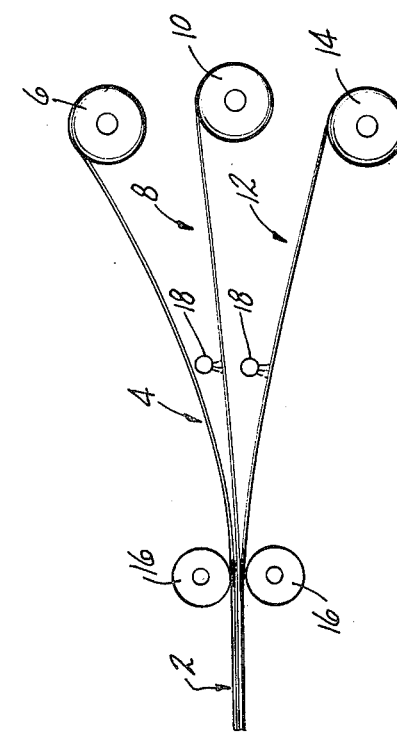
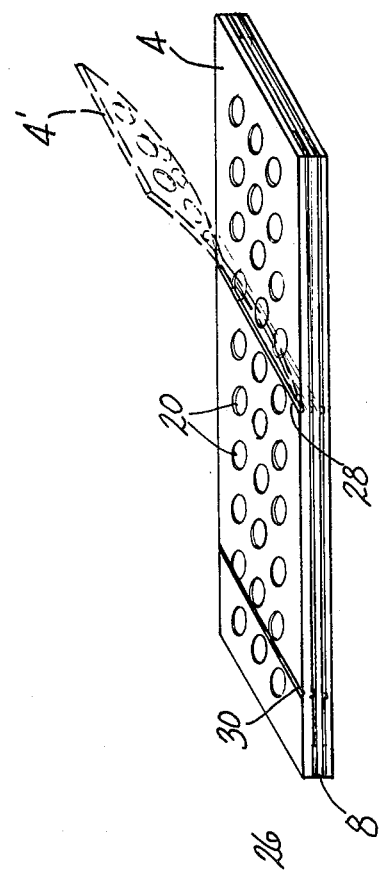
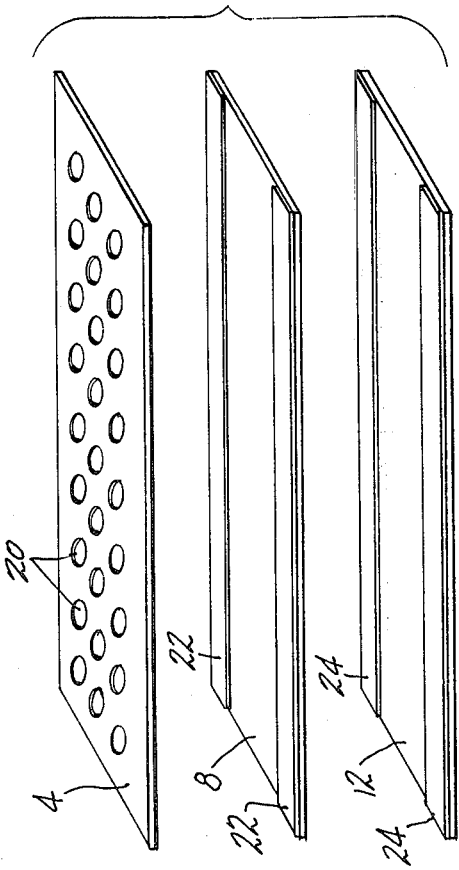

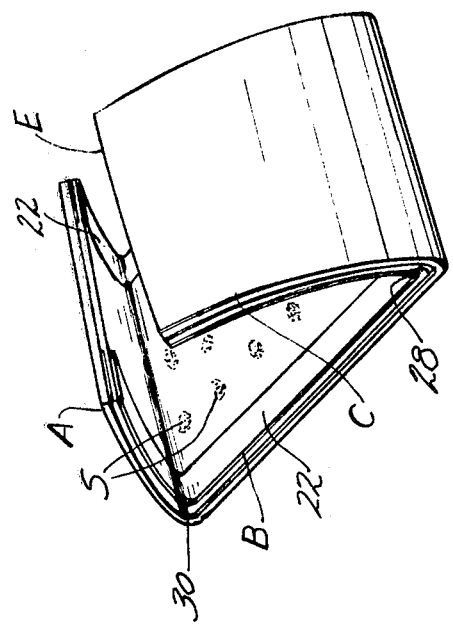
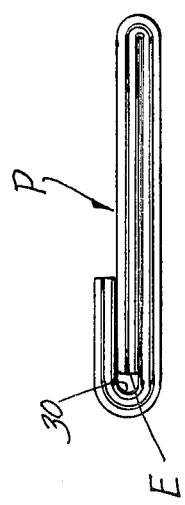
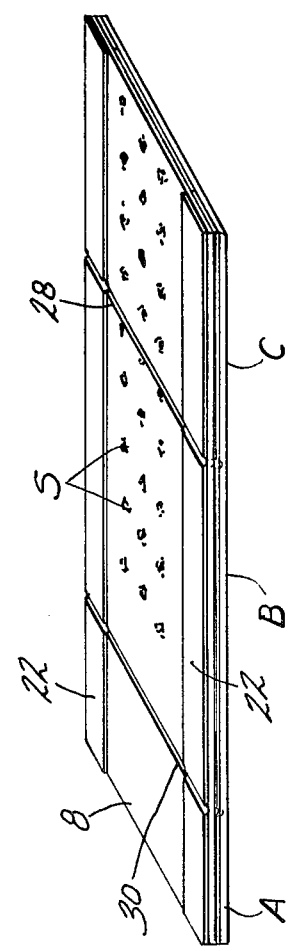

METHOD OF MAKING A STOOL SAMPLING DEVICE

This invention relates to a device for use in obtaining direct anal stool smears, and constitutes a continuation-in-part of my copending applications Ser. Nos. 110,437, filed Jan. 7, 1980, U.S. Pat. No. 4,273,741; and 203,083, filed Nov. 3, 1980, U.S. Pat. No. 4,367,750.

A procedure which is routinely performed in physicians' offices in connection with physical examinations involves the testing of the patient's stool for the presence of occult blood. The physician typically will obtain a sample of the patient's stool by probing the patient's rectum with a rubber glove. The sample which is thus obtained is typically tested with guiac and hydrogen peroxide reagents, which, in the presence of occult blood in the stool sample, will produce a characteristic blue coloration on the paper onto which the stool is smeared.

The obvious discomfort attendant to this type of stool sample gathering has produced a number of alternatives in the prior art. These alternatives involve paraphenalia which the patient takes home from the physician's office, and which the patient uses in the privacy of his home to obtain the stool sample, which is then transmitted back to the physician's office for the testing. This paraphenalia will include a specimen holder of some type, and a device, usually a wooden stick, for obtaining a stool sample after defecation. The sample is obtained from the toilet after defecation and transferred to the specimen holder, which is then returned to the physician's office. The stick is discarded after the stool sample is obtained. U.S. Pat. Nos. 3,996,006, issued Dec. 7, 1976; 4,092,120, issued May 30, 1978; and 4,199,550, issued Apr. 22, 1980 are illustrative of such prior art stool sampling devices.

There are disclosed in the aforementioned applications, and in my U.S. Pat. No. 4,259,964, issued Apr. 7, 1981, improved stool sampling devices which may be used in private by the patient at home, and which are used in the same manner as toilet paper to obtain the needed stool sample. These improved stool sampling devices are made of a laminate of pliant materials which can simply be drawn across the anus to obtain the stool smear after defecation. The laminate is then folded into a closed pouch and returned to the physician's office for testing. Basically, the laminate includes an outer layer of impervious pliant plastic such as polyethylene, which is preferably transparent, a middle layer of absorbent material, such as filter paper, onto which the stool sample is deposited, and an opposite outer screening layer of pliant material, such as polyvinyl alcohol polymer, which is preferably provided with a plurality of openings which serve to volumetrically control the amount of stool deposited on the middle absorbent layer. The various layers are adhesively secured to each other, with the screening layer being removable and discardable in the toilet after use of the device, and with the adhesive layer beneath the screening layer serving as the vehicle whereby the laminate can be folded into a pouch.

The stool sampling device disclosed in this application is an improvement of the aforesaid pliant laminate, which provides the same general advantages but at a lower manufacturing cost.

It has been determined that a laminated device of the type described above is most inexpensively manufactured when it is produced from continuous strips of material which are laminated together and then cut laterally into individual stool sampling devices.

To that end, the improved stool sampling device of this invention is formed from a continuous strip of impervious, pliant, transparent plastic which forms the first outer layer of the laminate; a continuous strip of absorbent material which forms the middle stool-receiving layer, and which is adhered to the impervious, transparent layer; and a continuous strip of the screening material layer, which is preferably perforated along its entire mid-axial portion. A pair of parallel lateral adhesive strips are deposited along the side edges of the continuous strip of absorbent material, which adhesive strips serve to releasably adhere the screening layer to the absorbent layer, and which also serve, after the screening layer has been removed and discarded, to provide means for securing the folded laminate into a closed pouch containing the stool sample. After the various strips are secured together, they are cut laterally to size to form the individual stool sampling devices, and each stool sampling device is provided with two transverse fold lines, one of which is spaced apart from one end edge of the device a distance substantially equal to the distance between the two fold lines thereby providing for the formation of a pouch with a closure flap in which the stool sample is held.

It is, therefore, an object of this invention to provide a device for obtaining stool samples for testing for the presence of occult blood, which device is usable by one in the privacy of the home in the same manner as toilet paper after defecation.

It is a further object of this invention to provide a device of the character described which is readily formed from continuous strips of pliant material which are laminated together to form a laminated stock from which individual stool sampling devices may be cut.

It is an additional object of this invention to provide a device of the character described which includes transverse fold lines and parallel adhesive means co-operable to form a closed pouch when the device is folded after the stool sample is obtained.

It is another object of this invention to provide a device of the character described which can be mass produced at low manufacturing cost.

These and other objects and advantages of this invention will become more readily apparent from the following detailed description of a preferred embodiment of the stool sampler formed in accordance with this invention when taken in conjunction with the accompanying drawings, in which:

FIG. 1 is a schematic representation of a manufacturing assembly suitable for forming, from continuous strip components, continuous strip stock suitable for cutting for forming the stool sampling devices of this invention;

FIG. 2 is an exploded view of fragments of the several strip components of the strip stock material from which the stool sampling device of this invention is formed;

FIG. 3 is an exploded view of the several components of a stool testing device formed in accordance with this invention, after the device has been cut from the stock strips;

FIG. 4 is a perspective view of the stool testing device of this invention, showing in phantom the mode of removal of the screening layer after the stool sample has been obtained;

FIG. 5 is a perspective view of the device of this invention after the screening layer has been removed;

FIG. 6 is a perspective view of the stool sampling device of this invention showing how the device is folded to form a closed pouch after the stool sample is taken; and FIG. 7 is a side view of the stool sampling device of this invention after it has been folded into a pouch.

Referring now to the drawings, there is disclosed in FIG. 1 a somewhat schematic representation of the manner in which the stock laminate used to form the sampling devices of this invention is produced. The stock laminate is formed as a continuous strip which is cut to size after lamination. The strip laminate 2 is formed by feeding a strip 4 of the screening material layer from a roll 6 thereof, a strip 8 of the absorbent material from a roll 10 thereof, and a strip 12 of a transparent impermeable plastic material from a roll 14 thereof, through a pair of opposed pressure rolls 16. Adhesive applicating devices 18 are used to apply adhesive to the transparent impermeable plastic strip 12 and to the absorbent material strip 8 to provide a bond for the laminate 2. The adhesive applicating devices can take the form of brushes, rollers, sprays, or double-sided adhesive tape strips fed from rolls.

As will be noted from FIG. 2, the screening layer 4 is formed with a plurality of openings 20 extending in columns of rows along the mid-axial portion of the layer 4. The openings 20 serve to volumetrically control the amount of stool deposited on the absorbent layer 8 when the device is used. The adhesive disposed on the absorbent layer 8 preferably takes the form of a pair of parallel strips 22 which extend along the side edge portions of the layer 8 so that the mid portion of the layer 8 is free of adhesive. Likewise, the transparent, impermeable plastic layer 12 preferably includes parallel strips 24 of adhesive which extend along the side edge portions of the layer 12 so that the mid portion of the layer 12 is free of adhesive. The adhesive strips 22 and 24 are preferably releasable, as will be discussed hereinafter.

Once the laminate 2 has been formed, after passing through the rolls 16, the laminate 2 is cut transversely into individual stool sampling devices 26, as shown in FIG. 3. It will be noted that the openings 20 extend through the entire axial extent of the screening layer 4 so that stool will be deposited on the absorbent layer 8 no matter where along the device the rectum is wiped. The layer 12 is impermeable so as to retain bacteria in the stool, and is transparent so that the chemical reaction can be viewed through the layer 12. The adhesive strips 24 are preferably restricted to the sides of the strip 12 so that the coloration will be clearly visible through the layer 12 without interference from adhesive.

Once the device has been laminated and cut to size, a pair of transverse fold lines 28 and 30 are formed in the device. These fold lines should preferably be formed as sharply as possible so as to aid in forming a closed pouch which will contain the stool sample for transmittal to the physician's office as tightly as possible, so that the possibility of bacterial escape from the stool sample is minimized. As noted in FIG. 4, after the device is used, the releasable adhesive strips 22 allow the screening layer 4 to be peeled off of the laminate, as indicated by 4', and discarded in the toilet by the user. It will be appreciated that the screening layer 4 acts, by means of the openings 20, to control the amount of stool which is deposited on the absorbent layer 8.

Referring to FIG. 5, it will be noted that, after the device has been used, and the screening layer 4 has been removed, there are a plurality of volumetric stool smears S deposited on the absorbent layer 8. The diameter of the openings 20, and the thickness of the screening layer 4 combine to control the volume of the stool smears S. When the screening layer 4 has been removed, the adhesive strips 22 are exposed so that the fold lines 28 and 30 can be used to from the pouch, as shown in FIGS. 6 and 7.

To form the pouch, the layers 8 and 12 are folded along the fold lines 28 and 30, as shown in FIG. 6, until the closed pouch P is formed, as shown in FIG. 7. It will be understood that the adhesive strips 22 hold the folded laminate together to keep the pouch P closed. At the same time, the edge E of the laminate is spaced apart from the fold line 28 a predetermined distance so that, when the pouch P is formed, the edge E is tightly juxtaposed with the fold line 30 so that the stool smears S are contained with a relatively tightly closed pouch P thereby minimizing the possibility of escape of bacteria and odor from the interior of the pouch.

If the absorbent layer 8 is pre-impregnated with guiac reagent, it will be appreciated that the screening layer 4 and its openings 20 will not allow the guiac to substantially penetrate the screening layer 4 prior to or during use of the device, thus possible adverse effects of the guiac on the patient are virtually eliminated. Of course, the device may be produced with a non guiac-impregnated absorbent layer, however, if the guiac-impregnated layer is used, then the hydrogen peroxide is the only reagent which need be applied in the physician's office to perform the test. When the pouch containing the stool sample is received in the physician's office, the adhesive strips 22 can be disrupted so that the technician can peel open the pouch to apply the necessary reagents. The adhesive used is one which provides for resealability after the reagents are applied to the stool sample.

Preferably, the impermeable layer 12 will be made of transparent plastic material so that, once the necessary reagents are applied to the stool spots S, the pouch may be reclosed and the presence or absence of the characteristic blue color may be observed through the impermeable layer 12.

As previously noted, the adhesive strips 24 can be formed from a releasable adhesive so that the absorbent layer 8 can be peeled off of the impermeable layer 12. The separated absorbent layer 8 bearing the stool spots S can then be used in chromatographic testing of the stool specimen.

The patient will be instructed to use the device in such a manner that the stool smear will extend from section B toward section C of the device, and so that no stool will be deposited on section A. In forming the pouch P, section C will be folded first to entrap all of the stool on the device within the confines of juxtaposed sections B and C. The stool-free section A will then be folded down over sections B and C to form the outer, uncontaminated closure for the pouch P.

After the test has been performed, the closed pouch may be discarded with minimal chance of bacterial pollution from the enclosed stool sample.

It will be readily appreciated that the stool sampling device of this invention can be economically manufactured from stock endless strip components, cut to size, and scored for folding. The use of the device is simple, natural and convenient for a patient, and the device may be readily folded, after use, into a closed pouch which can be easily reopened for application of reagents, and then refolded into a closed pouch once again. The device of this invention may also be used to collect other biological samples and contain them in a similar manner.

Since many changes and variations of the disclosed embodiment of the invention may be made without departing from the inventive concept, it is not intended to limit the invention otherwise than as required by the appended claims.

What is claimed is:

1. A method of forming a biological material sampling device, said method comprising the steps of:
   (a) providing a first roll of a pliant impermeable material;
   (b) providing a second roll of a pliant absorbent material;
   (c) providing a third roll of a pliant screening material;
   (d) feeding material from said first, second and third rolls into overlying relationship;
   (e) applying strips of adhesive to edge portions of the surface of said pliant, impermeable material adjacent to said pliant absorbent material;
   (f) applying strips of a releasable, reusable material to the edge portions of the surface of said pliant, absorbent material adjacent to said pliant screening material;
   (g) bonding said pliant, impermeable material, said pliant, absorbent material and said pliant screening material to form a laminate;
   (h) forming transverse fold lines on said laminate; and
   (i) cutting said laminate transversely to form individual sampling devices.

2. The method of claim 1, wherein said cutting step is performed at predetermined locations whereby each of said individual sampling devices will include two transverse fold lines with one of said fold lines being spaced apart from one end edge of said device approximately the same distance as the distance between each of said fold lines in the device.

3. The method of claim 2 wherein said adhesive is a releasable, reusable material.

* * * * *